United States Patent [19]

Brouwer et al.

[11] Patent Number: 4,567,295
[45] Date of Patent: Jan. 28, 1986

[54] COMPOSITION ACTIVE AGAINST MITES, WHITEFLY AND THRIPS, PHARMACEUTICAL COMPOSITION, AND NEW BENZOYLUREA COMPOUNDS

[75] Inventors: Marius S. Brouwer; Arnoldus C. Grosscurt, both of Weesp, Netherlands

[73] Assignee: Duphar International Research B.V., Weesp, Netherlands

[21] Appl. No.: 572,144

[22] Filed: Jan. 19, 1984

[30] Foreign Application Priority Data

Jan. 24, 1983 [NL] Netherlands ............ 8300237

[51] Int. Cl.$^4$ ........................... C07G 127/19
[52] U.S. Cl. ....................... 564/44; 514/594
[58] Field of Search ............ 564/44; 514/594

[56] References Cited

U.S. PATENT DOCUMENTS 4,350,706 9/1982 Brouwer et al. ............ 564/44

FOREIGN PATENT DOCUMENTS 2106499 4/1983 United Kingdom ............ 564/44

Primary Examiner—Charles F. Warren
Assistant Examiner—R. A. Picard
Attorney, Agent, or Firm—Stevens, Davis, Miller & Mosher

[57] ABSTRACT

The invention relates to a composition active against mites, whitefly and thrips, which comprises, in addition to a liquid or solid inert carrier material, a benzoylurea compound of the general formula

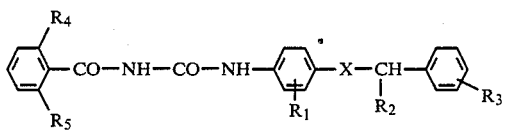

wherein $R_1$ is hydrogen atom or represents 1 or 2 substituents which are selected from the group consisting of chlorine, methyl and trifluoromethyl, $R_2$ is an alkyl group having 2–4 carbon atoms or a cycloalkyl group having 3 or 4 carbon atoms, $R_3$ is a hydrogen atom or represents 1–3 substituents which are selected from the group consisting of halogen, and alkyl, alkoxy, haloalkyl and haloalkoxy having 1–4 carbon atoms, $R_4$ and $R_5$ are both fluorine atoms, or wherein $R_4$ is a chlorine atom and $R_5$ is a hydrogen atom, and X is an oxygen or sulphur atom.

The composition may be used in a dosage of 10 to 5000 g of active substance per hectare.

The invention further relates to pharmaceutical compositions comprising the above compounds. Finally the invention relates to new benzoylurea compounds and to the preparation thereof.

3 Claims, No Drawings

COMPOSITION ACTIVE AGAINST MITES, WHITEFLY AND THRIPS, PHARMACEUTICAL COMPOSITION, AND NEW BENZOYLUREA COMPOUNDS

The invention relates to a composition active agaist mites, whitefly and thrips, and to a method of preparing this composition. The invention also relates to the use of this composition for controlling mites, whitefly and thrips. Further the invention relates to new benzoylurea compounds and to the preparation thereof. Finally the invention relates to pharmaceutical compositions comprising benzoylurea compounds and to the use of these compositions for combating tumors.

N-Benzoyl-N'-phenylurea compounds having insecticidal activity are known from applicants' Netherlands patent application No. 7105350. In Chem. Abstracts 91, 20141 (1979) benzoylurea compounds are described having both an insecticidal and an acaricidal activity, for example N-(2,6-difluorobenzoyl)-N'-(4-benzyloxyphenyl)urea. This compound, however, proves to have no marked acaricidal activity in practically acceptable dosages. Two noxious insects are whitefly and thrips. These insects generally cannot be controlled easily and therefore occupy a special place among the insects. The above-mentioned benzoylurea compound, viz. N-(2,6-difluorobenzoyl)-N'-(4-benzyloxyphenyl)urea, also has no marked activity on whitefly and thrips.

It has surprisingly been found, that benzoylurea compounds of the general formula

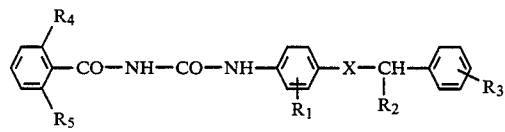

(I)

wherein
$R_1$ is a hydrogen atom or represents 1 or 2 substituents which are selected from the group consisting of chlorine, methyl or trifluoromethyl,
$R_2$ is an alkyl group having 2–4 carbon atoms or a cycloalkyl group having 3 or 4 carbon atoms,
$R_3$ is a hydrogen atom or represents 1–3 substituents which are selected from the group consisting of halogen, and alkyl, alkoxy, haloalkyl and haloalkoxy having 1–4 carbon atoms,
$R_4$ and $R_5$ are both fluorine atoms, or wherein $R_4$ is a chlorine atom and $R_5$ is a hydrogen atom, and
X is an oxygen or sulphur atom,
have a strong acaricidal activity, and in addition are able to control whitefly and thrips effectively.

These compounds are generally known from the applicants' Netherlands patent application No. 7905155. The compounds mentioned in this patent application have a strong insecticidal activity. An activity against mites, whitefly and thrips, hoever, has not been proved. On the contrary, one of the compounds with the strongest insecticidal activity, known from this patent application, viz. N-(2,6-difluorobenzoyl)-N'-[4-(1-phenylethoxy)phenyl]urea, shows no or substantially no marked activity on mites, whitefly and thrips.

Of the above compounds those compounds prove to be most suitable to be used for controlling mites, whitefly and thrips, which correspond to the general formula

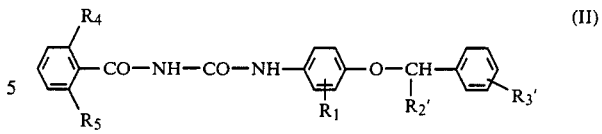

(II)

wherein
$R_1$, $R_4$ and $R_5$ have the above meanings,
$R_2$ is a n-propyl, isopropyl or cyclopropyl group, and
$R_3'$ is a hydrogen atom or represents 1 or 2 substituents which are selected from the group consisting of halogen and haloalkyl and haloalkoxy having 1–4 carbon atoms.

Of the last-mentioned compounds N-(2,6-difluorobenzoyl)-N'-[4-(α-cyclopropyl-4-chlorobenzyloxy)phenyl]urea (1) has the broadest activity spectrum with regard to mites, whitefly and thrips, and therefore is to be preferred.

Other examples of benzoylurea compounds to be used successfully for controlling mites, whitefly and thrips are:
(2) N-(2,6-difluorobenzoyl)-N'-[4-(1-phenylisobutoxy)-phenyl]urea;
(3) N-(2,6-difluorobenzoyl)-N'-[4-{1-(4-trifluoromethylphenyl)pentyloxy}-phenyl]urea;
(4) N-(2,6-difluorobenzoyl)-N'-[4-(1-phenylbutoxy)-phenyl]urea;
(5) N-(2,6-difluorobenzoyl)-N'-[4-{1-(4-chlorophenyl)isobutoxy}-phenyl]-urea;
(6) N-(2,6-difluorobenzoyl)-N'-[4-(1-phenylpropoxy)-phenyl]urea;
(7) N-(2,6-difluorobenzoyl)-N'-[3-chloro-4-(1-phenylpropoxy)phenyl]urea;
(8) N-(2,6-difluorobenzoyl)-N'-[4-{1-(4-chlorophenyl)-propoxy}phenyl]urea;
(9) N-(2-chlorobenzoyl)-N'-[3-methyl-4-{1-(4-chlorophenyl)isobutoxy}-phenyl]urea;
(10) N-(2,6-difluorobenzoyl)-N'-[3-methyl-4-{1-(4-chlorophenyl)isobutoxy}-phenyl]urea;
(11) N-(2,6-difluorobenzoyl)-N'-[3-chloro-4-{1-(2,4-dichlorophenyl)butoxy}-phenyl]urea;
(12) N-(2-chlorobenzoyl)-N'-[3-methyl-4-{1-(2,4-dichlorophenyl)butoxy}-phenyl]urea;
(13) N-(2,6-difluorobenzoyl)-N'-[3-methyl-4-{1-(2,4-dichlorophenyl)butoxy}-phenyl]urea;
(14) N-(2,6-difluorobenzoyl-N'-[3-chloro-4-}1-(4-trifluoromethylphenyl)-isobutoxy}phenyl]urea;
(15) N-(2,6-difluorobenzoyl)-N'-[3-chloro-4-{1-(4-methoxyphenyl)isobutoxy}-phenyl]urea;
(16) N-(2,6-difluorobenzoyl)-N'-[3-chloro-4-{1-(4-chlorophenyl)isobutoxy}-phenyl]urea;
(17) N-(2,6-difluorobenzoyl)-N'-[4-{1-(4-fluorophenyl)isobutoxy}phenyl]urea;
(18) N-(2,6-difluorobenzoyl)-N'-[4-{1-(3,4-dichlorophenyl)isobutoxy}-phenyl]urea;
(19) N-(2,6-difluorobenzoyl-N'-[4-{1-(3,4-dimethylphenyl)isobutoxy}-phenyl]urea;
(20) N-(2,6-difluorobenzoyl)-N'-[4-{1-(4-1,1,2,2-tetrafluoroethoxyphenyl)-isobutoxy}phenyl]urea;
(21) N-(2,6-difluorobenzoyl)-N'-[3-chloro-4-{1-(4-chlorophenyl)propylthio}-phenyl]urea; and
(22) N-(2,6-difluorobenzoyl)-N'-[4-{1-(4-chlorophenyl)-propylthio}phenyl]-urea.

The active substances according to the invention can be used for the control of mites, whitefly and thrips in agriculture, horticulture and forestry, as well as against mites in the veterinary and medical-hygienic sector. The compounds are especially active against larvae and eggs of mites, whitefly and thrips. In addition it has been found that the compounds mentioned above have cytostatic or anti-tumor activity, in that they show an inhibiting effect on the growth of tumors. For use in pharmaceutical compositions for combating tumors in living beings the compounds of the invention should be incorporated into pharmaceutically acceptable carriers. For practical pesticidal application the substances in accordance with the invention are usually processed to compositions. In such compositions the active substance is mixed with solid carrier material or dissolved or dispersed in liquid carrier material, if desired in combination with auxiliary substances, for example, emulsifiers, wetting agents, dispersible agents and stabilizers.

Examples of compositions according to the invention are aqueous solutions and dispersions, oily solutions and oily dispersions, solutions in organic solvents, pastes, dusting powders, dispersible powders, miscible oils, granules, pellets, invert emulsions, aerosol compositions and fumigating candles.

Dispersible powders, pastes and miscible oils are compositions in concentrate form which are diluted prior to or during use.

The invert emulsions and solutions in organic solvents are mainly used in air application, namely when large areas are treated with a comparatively small quantity of composition. The invert emulsion can be prepared shortly before or even during spraying in the spraying apparatus by emulsifying water in an oily solution or an oily dispersion of the active substance. The solutions of the active substance in organic solvents may be provided with a phytotoxicity-reducing substance, for instance, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, if desired in the presence of a binder, on granular carrier material, for example porous granules (for example pumice and attaclay), mineral non-porous granules (sand or ground marl), organic granules (for example, dried coffee grounds, cut tobacco stems and ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then with liquid to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromatics, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight. In addition to a miscible oil may also be mentioned as a liquid and highly concentrated primary composition a solution of the active substance in a readily water-miscible liquid, for example, a glycol, or glycol ether, to which solution a dispersion agent and, if desired, a surface-active substance has been added. When diluting with water shortly before or during spraying, an aqueous dispersion of the active substance is then obtained.

An aerosol composition according to the invention is obtained in the usual manner by incorporating the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example, a lubricant, e.g., calcium stearate or magnesium stearate, may be added to a dispersible powder or a mixture to be granulated. "Adhesives", for example, polyvinylalcohol, cellulose derivatives or other colloidal materials, such as casein, may also be added so as to improve the adhesion pf the pesticide to the crop. Furthermore, a substance may be added to reduce the phytotoxicity of the active substance which is a carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

For use in such a combination composition are to be considered the following known insecticidal, acaricidal and fungicidal compounds.

Insecticides, for example:
1. organic chlorine compounds, for example 6,7,8,9,10,10-hexachloro-1,5,5a,6,9,9a-hexahydro-6,9-methano-2,4,3-benzo[e]-dioxathiepine-3-oxide;
2. carbamates, for example, 2-dimethylamino-5,6-dimethylpyrimidin-4-yl dimethyl carbamate and 2-isopropoxyphenyl methylcarbamate;
3. di(m)ethylphosphates, for example, 2-chloro-2-diethylcarbamoyl-1-methylvinyl-, 2-methoxycarbonyl- 1-methylvinyl-, 2-chloro-1-(2,4-dichlorophenyl)vinyl-, and 2-chloro-1-(2,4,5-trichlorophenyl)vinyl di(m)ethyl phosphate;
4. O,O-di(m)ethyl phosphorothioates, for example, O(S)-2-methylthioethyl-, S-2-ethylsulphinylethyl-, S-2-(1-methylcarbamoylethylthio)ethyl-, O-4-bromo-2,5-dichlorophenyl-, O-3,5,6-trichloro-2-pyridyl-, O-2-isopropyl-6-methylpyrimidin-4-yl-, and O-4-nitrophenyl O,O-di(m)ethyl phosphorothioate;
5. O,O-di(m)ethyl phosphorodithioates, for example, S-methylcarbamoylmethyl-, S-2-ethylthioethyl-, S-(3,4-dihydro-4-oxobenzo[d]-1,2,3-triazin-3-ylmethyl)-, S-1,2-di(ethoxycarbonyl)ethyl-, S-6-chloro-2-oxobenzoxazolin-3-ylmethyl-, and S-2,3-dihydro-5-methoxy-2-oxo-1,3,4-thiadiazol-3-ylmethyl O,O-di(m)ethylphosphorodithioate;
6. phosphonates, for example, dimethyl 2,2,2-trichloro-1-hydroxyethylphosphonate;
7. natural and synthetic pyrethroids;
8. amidines, for example, N'-(2-methyl-4-chlorophenyl)-N,N-dimethylformamidine;
9. microbial insecticides, such as *Bacillus thuringiensis*,
10. carbamoyl-oximes, such as S-methyl N-(methylcarbamoyloxy)thiacetamidate; and
11. other benzoylurea compounds, such as N-(2,6-difluorobenzoyl)-N'-(4-chlorophenyl)urea.

Acaricides, for example:
1. organic tin compounds, for example, tricyclohexyl tin hydroxide and di[tri-(2-methyl-2-phenylpropyl)tin]oxide;
2. organic halogen compounds, for example isopropyl 4,4'-dibromobenzilate, 2,2,2-trichloro-1,1-di(4-chlorophenyl)ethanol and 2,4,5,4'-tetrachlorodiphenyl sulphone;
3. synthetic pyrethroids,
and furthermore: 3-chloro-α-ethoxyimino-2,6-dimethoxybenzyl benzoate and O,O-dimethyl S-methylcarbamoyl methyl phosphorothioate.

Fungicides, for example:
1. organic tin compounds, for example, triphenyl tin hydroxide and triphenyl tin acetate;
2. alkylene bisdithiocarbamates, for example, zinc ethylenebisdithiocarbamate and manganese ethylene bisdithiocarbamate;
3. 1-acyl- or 1-carbamoyl-N-benzimidazole(-2)carbamates and 1,2-bis(3-alkoxycarbonyl-2-thiureido)benzene,
and furthermore 2,4-dinitro-6-(2-octylphenylcrotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidinemethanol, 1-(isopropylcarbamoyl)-3-(3,5-dichlorophenyl)hydantoin, N-(1,1,2,2-tetrachloroethylthio)-4-cyclohexene-1,2-carboximidine, N-trichloromethylmercapto-4-cyclohexene-1,2-dicarboximidine, N-tridecyl-2,6-dimethylmorpholine. The dosages of the pesticidal composition according to the invention desired for practical application will, of course, depend on various factors, for example, application area, selected active substance, form of application, nature and extent of the infection, and the weather conditions. In general favourable results are achieved with a dosage corresponding to 10–5000 g of the active substance per hectare.

A part of the above-mentioned compounds is known from the Netherlands patent application no. 7905155 mentioned before. The other compounds are new. Consequently the invention also relates to new benzoylurea compounds having the general formula

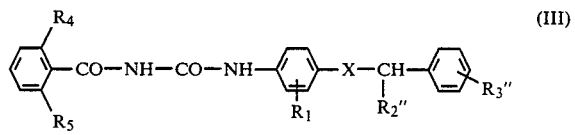

wherein $R_1$, $R_4$ and $R_5$ and X have the meaning mentioned before, $R_2''$ is an ethyl, n-propyl, isopropyl, or cyclopropyl group, and $R_3''$ represents 1 or 2 substituents, selected from the group consisting of halogen, and alkyl, alkoxy, haloalkyl and haloalkoxy having 1–4 carbon atoms.

The new compounds can be prepared in a manner known per se for the preparation of related compounds, for example, according to the preparation of related compounds, for example, according to one of the methods described in the before-mentioned Netherlands patent application no. 7905155 or according to the methods described in the Netherlands patent applications Nos. 7806678 or 8005588. For example, the above new compounds can be prepared by (a) reaction of a substituted aniline of the general formula

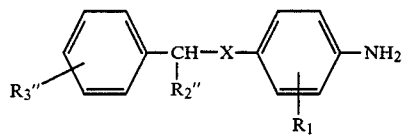

with a benzoylisocyanate of the general formula

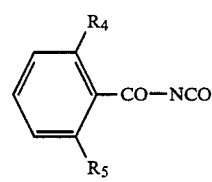

or (b) reaction of an isocyanate of the general formula

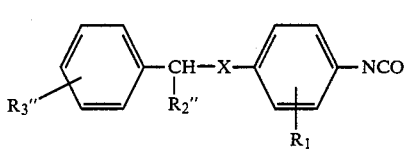

with a benzamide of the general formula

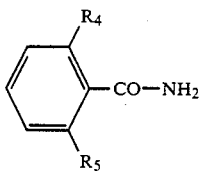

or (c) reaction of a halide of the general formula

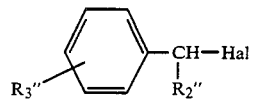

with a compound of the general formula

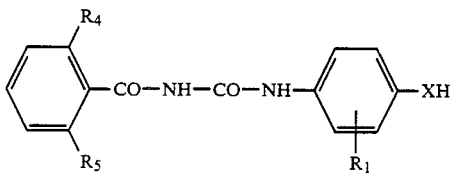

In the above formulas Hal represents a halogen atom and X, $R_1$, $R_4$, $R_5$, $R_2''$ and $R_3''$ have the above meanings. The reactions mentioned sub (a) and sub (b) are preferably carried out in the presence of an organic solvent, such as an aromatic hydrocarbon, an alkyl halide, a cyclic or non cyclic dialkyl ether, or acetonitrile, at a reaction temperature between 0° C. and the boiling point of the solvent used. The reaction mentioned sub (c) is preferably carried out under the influence of a base in a polar organic solvent which is inert with regard to reaction components and final product. The last-mentioned reaction is also preferably carried out at a temperature between 0° C. and the boiling point of the solvent used. This reaction can also be accomplished in the presence of a catalytic amount of a metal-complex.

The invention will now be described in more detail with reference to the following specific examples.

EXAMPLE I

Preparation of N-(2,6-difluorobenzoyl)-N'-[4-(α-cyclopropyl-4-chlorobenzyloxy)phenyl]urea (1)

1,57 g of 2,6-difluorobenzoylisocyanate was added to a solution of 3,35 g 4-(α-cyclopropyl-4-chlorobenzyloxy)aniline in 30 ml of dry acetonitrile while stirring. After stirring for 1 hour at room temperature the formed precipitate was sucked off, washed with acetonitrile, and dried. The desired product was obtained in a yield of 2.90 g; melting point 185°–188° C. The structure was confirmed by means of CMR.

The starting aniline compound was obtained from the corresponding nitro compound by reduction with hydrogen under the influence of Raney nickel as a catalyst; ethyl acetate was used as a solvent. 1-Nitro-4-(α-cyclopropyl-4-chlorobenzyloxy)benzene was prepared by a reaction of α-cyclopropyl-4-chlorobenzylalcohol with 1-fluoro-4-nitrobenzene in dimethylformamide as a solvent and in the presence of a sodiumhydride dispersion. The substituted benzylalcohol was obtained by a reduction of the corresponding ketone under the influence of lithiumaluminiumhydride. In a corresponding manner, in which if desired, instead of acetonitrile diethylether was used as a solvent for the urea-formation, the following compounds were prepared; the compound members correspond with the numbers given before in this specification:

| compound no. | melting point | compound no. | melting point |
|---|---|---|---|
| (5) | 166–172° C. | (13) | 131–133° C. |
| (8) | 171–173° C. | (14) | 160–164° C. |
| (9) | 155–158° C. | (15) | 138–141° C. |
| (10) | 177–180° C. | (16) | 194–197° C. |
| (11) | 150–153° C. | (17) | 153–159° C. |
| (12) | 118–120° C. | (18) | 174–177° C. |
| (19) | 201–202° C. | (21) | 169–173° C. |
| (20) | 116–121° C. | (22) | 136–142° C. |

EXAMPLE II (a) Preparation of a solution of an active compound, viz. N-(2,6-difluorobenzoyl)-N'-[4-(α-cyclopropyl-4-chlorobenzyloxy)phenyl]urea, in a water-miscible liquid ("liquid")

10 g of the above active substance were dissolved in a mixture of 10 ml of isophorone and approximately 70 ml of dimethylformamide, after which polyoxyethylene glycol ricinyl ether was added as an emulsifier in a quantity of 10 g. In a corresponding manner the other active substances were processed to 10 or 20% "liquids". In a corresponding manner "liquids" were obtained in N-methylpyrrolidone, dimethylformamide, and a mixture of N-methylpyrrolidone and isophorone as solvents.

(b) Preparation of a solution of the active substance in an organic solvent 200 mg of the active substance to be tested were dissolved in 1,000 ml of acetone in the presence of 1,6 g of nonylphenolpolyoxyethylene. After pouring out into water this solution can be used as a spray liquid.

(c) Preparation of an emulsifiable concentrate of the active substance 10 g of the active substance to be tested were dissolved in a mixture of 15 ml of isophorone and 70 ml of xylene; to this solution were added 5 g of a mixture of a polyoxyethylene sorbitan ester and an alkyl benzene sulphonate as an emulsifier.

(d) Preparation of a dispersible powder (W.P.) of the active substance 25 g of the active substance to be tested were mixed with 68 g of kaolin in the presence of 2 g of sodium butylnaphthalene sulphonate and 5 g of lignin sulphonate.

(e) Preparation of a suspension concentrate (flowable) of the active substance

A mixture of 10 g of the active substance, 2 g of lignin sulphonate and 0.8 g of a sodium alkylsulphate were supplied with water till a total amount of 100 ml.

(f) Preparation of a granule of the active substance 7.5 g of the active substance, 5 g of sulphite lye and 87.5 g of ground dolomite were mixed, after which the resulting mixture was processed to a granular composition by means of the so-called compacting method.

EXAMPLE III

Dwarf French bean plants (*Phaseolus vulgaris*) having two well developed leaves were infected with *Tetranychus cinnabarinus* (carnation spider mite) by placing a fixed number of adult female mites on the plants. Two days after the infection the plants with the adult mites present thereon were sprayed until dripping with compositions obtained according to Example II(b) in various concentrations; in addition approx. 150 mg of an alkylated phenolpolyoxyethylene compound (Citowett) per liter had been added. Five days after the spraying the adult mites were removed from the plants. The plants were stored during two weeks in a room with controlled temperature (T) and humidity (RH), an alternating light-dark cycle of 16 hours light and 8 hours dark being used. Light: T. approx. 24° C., RH approx. 70%; dark: T approx. 19° C., RH 80–90%. Then the reduction of the population, i.e. the mortality of the number of adults, larvae and eggs in comparison with plants which had not been treated with chemicals, was established. The experiments were carried out in triplicate. The average results of the experiments are recorded in Table A below. The meanings of the symbols used in the table are as follows:

+ = 90–100% reduction of the population; plants free or substantially free from spider mites;
± = 50–90% reduction of the population;
− = <50% reduction of the population.

N-(2,6-difluorobenzoyl)-N'-(4-benzyloxyphenyl)urea and N-(2,6-difluorobenzoyl)-N'-[4-(1-phenylethoxy)-phenyl]urea included in the tests by way of comparison.

TABLE A

Activity against *Tetranychus cinnabarinus* (carnation spider mite) known: (a) N—(2,6-difluorobenzoyl)-N'—(4-benzyloxyphenyl)urea; (b) N—(2,6-difluorobenzoyl)-N'—[4-(1-phenylethoxy) phenyl]urea.

| compound nr. | concentration in mg of act. ingred. per liter | | | | | | |
|---|---|---|---|---|---|---|---|
|  | 300 | 100 | 30 | 10 | 3 | 1 | 0,3 |
| (1) | + | + | + | + | − | | |
| (2) | + | + | + | + | + | ± | − |
| (3) | + | + | + | ± | − | | |
| (4) | + | + | + | + | + | − | |
| (5) | + | + | + | + | − | | |
| (6) | + | + | ± | ± | − | | |
| (7) | + | ± | ± | − | | | |
| (8) | + | − | | | | | |
| (9) | + | + | + | + | − | | |
| (10) | + | + | + | + | + | − | |
| (11) | + | + | + | + | ± | − | |
| (12) | + | + | + | + | ± | − | |
| (13) | + | + | + | + | + | | |
| (14) | + | + | + | + | − | | |
| (15) | + | + | + | + | − | | |
| (16) | + | + | + | + | − | | |
| (a) | − | | | | | | |
| (b) | − | | | | | | |

In practice insecticidal and acaricidal compositions are used in quantities of approx. 1000 liters per hectare. The coverage of the plants with the composition, however, is considerably less in practice than in a laboratory or greenhouse experiment as described above. Accordingly, it has proven that in practice the dosage should be improved by a factor of 10 to achieve the same efficiency. Therefore in practical application the above quantities with acaricidal activity correspond to approx. 10 to approx. 3000 g of active substance per hectare. Repetitions of the above experiments, wherein the adult mites were removed prior to the spraying (method A), or wherein the spraying was carried out prior to the infection (Method B), yielded about the same results.

EXAMPLE IV

In the same way as described in Example III, method A, benzoylurea compounds according to the invention were tested on *Panonychus ulmi* (European red mite). The results are recorded in table B, wherein the symbols have the same meanings as in Example III.

TABLE B

Activity against *Panonychus ulmi* (European red mite).

| compound no. | concentration in mg of act. ingred. per liter | | | | |
|---|---|---|---|---|---|
|  | 300 | 100 | 30 | 10 | 3 |
| (1) | + | + | + | + | − |
| (4) | ± | ± | − | | |
| (7) | + | + | ± | | |
| (13) | + | + | + | − | |

Liquid compositions are applied on fruit-trees in quantities of approx. 1500 liters per hectare. Then the above quantities with acaricidal activity correspond in practice to approx. 150 to approx. 4500 grams of active substance per hectare. When the spraying was carried out prior to the infection of the plant (method B) about the same results were obtained.

EXAMPLE V

In the same way as indicated in Example III, method A, benzoylurea compounds according to the invention were tested on *Tetranychus urticae* (two-spotted spider mite), giving the results recorded in Table C. Again the meanings of the symbols are the same as in Example III.

TABLE C

Activity against *Tetranychus urticae* (two-spotted spider mite)

| compound no. | concentration in mg of act. ingred. per liter | | | | | | |
|---|---|---|---|---|---|---|---|
|  | 300 | 100 | 30 | 10 | 3 | 1 | 0,3 |
| (1) | + | + | + | ± | − | | |
| (2) | + | + | + | + | + | ± | − |
| (3) | + | + | + | ± | − | | |
| (4) | + | + | + | + | + | − | |

About the same results were found, when the spraying was carried out prior to the infection (method B), and when was tested on a multiresistent strain of *Tetranychus urticae*. In practice the above quantities with acaricidal activity correspond to approx. 10 to approx. 3000 g of active substance per hectare.

EXAMPLE VI

In the same way as indicated in Example III, method B, benzoylurea compounds according to the invention were tested in comparison with the known compounds (a) and (b) on *Trialeurodes vaporariorum* (whitefly). The results recorded in table D were obtained. The meanings of the symbols are the same again as in Example III. See also Example III for the meanings of (a) and (b). In case the results do not finish with a "−" sign, the tests have not been completed.

TABLE D

Activity against *Trialeurodes vaporariorum* (whitefly).

| compound no. | concentration in mg of act. ingred. per liter | | | | |
|---|---|---|---|---|---|
|  | 300 | 100 | 30 | 10 | 3 |
| (1) | + | + | + | ± | − |
| (4) | + | + | + | + | ± |
| (5) | + | ± | − | | |

TABLE D-continued

Activity against *Trialeurodes vaporariorum* (whitefly).

| compound no. | concentration in mg of act. ingred. per liter | | | | |
|---|---|---|---|---|---|
| | 300 | 100 | 30 | 10 | 3 |
| (6) | + | | | | |
| (7) | + | | | | |
| (8) | + | + | + | + | |
| (a) | − | | | | |
| (b) | ± | | | | |

In practice the above quantities with activity on whitefly correspond to approx. 100 to approx. 3000 g of active substance per hectare.

EXAMPLE VII

In the same way as indicated in Example III, method A, benzoylurea compounds according to the invention were tested in comparison with the known compounds (a) and (b) on thrips. The results recorded in table E were obtained. The meanings of the symbols are the same again as in Example III. See also Example III for the meanings of (a) and (b); and Example VI.

TABLE E

Activity against thrips.

| compound no. | concentration in mg of act. ingred. per liter | | | | | |
|---|---|---|---|---|---|---|
| | 300 | 100 | 30 | 10 | 3 | 1 |
| (1) | + | + | + | + | + | |
| (2) | + | + | + | + | + | + |
| (3) | + | + | + | + | + | |
| (4) | + | + | + | + | + | + |
| (5) | + | + | + | ± | ± | |
| (6) | + | + | ± | − | | |
| (7) | + | + | + | ± | − | |
| (8) | + | + | + | + | + | − |
| (a) | − | | | | | |
| (b) | − | | | | | |

About the same results were found when the spraying was carried out prior to the infection (method B). In practice the above quantities with activity on thrips correspond with approx. 10 to approx. 3000 g of active substance per hectare.

EXAMPLE VIII

Dwarf French bean plants (*Phaseolus vulgaris*) having two well developed leaves were sprayed from below and from above until dripping with a composition prepared according to Example II(a); in addition 150 mg of Citowett per liter had been added to this composition. The composition comprised a benzoylurea compound according to the invention as the active substance in various concentrations. After the plants had dried-up they were infected with mites of a multiresistant strain of *Tetranychus urticae* (two-spotted spider mite) in the same way as described in Example III. The experiments were carried out outdoors. After 24 days the reduction of the population with respect to infected plant material, which was not sprayed with a composition, was estimated. The experiments were carried out fivefold. The average results are recorded in table F.

TABLE F

Acaricidal activity against *Tetranychus urticae*

| compound no. | concentration in mg of act. ingred. per liter | reduction of the popul. after 24 days |
|---|---|---|
| (1) | 100 | 100 |
| | 30 | 98 |
| | 10 | 86 |
| (4) | 100 | 81 |

TABLE F-continued

Acaricidal activity against *Tetranychus urticae*

| compound no. | concentration in mg of act. ingred. per liter | reduction of the popul. after 24 days |
|---|---|---|
| | 30 | 60 |
| | 10 | 42 |

The quantities presented in table F correspond to approx. 100 to approx. 1000 g of active substance per hectare under practical conditions.

EXAMPLE IX

Apple trees, headed on 40 cm, were sprayed from below and from above until dripping with a composition prepared according to Example II(a); in addition 250 mg of an alkylated phenolpolyoxyethylene compound (Neutronix) per liter had been added to this composition. The composition comprised a benzoylurea compound according to the invention as an active substance. The apple trees were infected previously as described in Example III with *Aculus schlechtendali* (apple rust mite), and at the moment of spraying the mites were present in all development-stages. After 2 and 4 weeks outdoors the reduction of the population of the mites was established. The experiments were carried out sixfold. The average results are recorded in table G.

TABLE G

Acaricidal activity against *Aculus schlechtendali*

| compound no. | concentration in mg of act. ingred. per liter | reduction of the popul. after 2 wks | after 4 wks. |
|---|---|---|---|
| (1) | 100 | 93 | 62 |
| | 30 | 72 | 51 |
| untreated | — | 0 | 0 |

EXAMPLE X

Inhibition of the growth of tumor cells

After pre-incubation at 37° C. during 3 hours the compound to be tested was added in an amount of 5000 ppm to B 16 melanoma cells, growing as a monolayer on a growing medium. The experiment was carried out in triplicate. The mixture was then incubated at 37° C. during 20 hours. After removal of the growing-medium and the test-compound the cells were washed and fresh growing-medium was added. The amount of cells was determined 48 hours after the beginning of the incubation period with a microcell Coulter Counter. Compound no. (4) caused 16% inhibition of the cell growth compared to an experiment without a test-compound.

We claim:

1. A composition, active against mites, whitefly and thrips, characterized in that, in addition to a liquid or solid inert carrier material, the composition comprises a benzoylurea compound of the formula

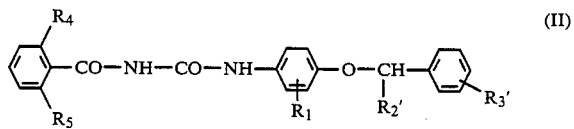

wherein $R_1$ is a hydrogen atom or represents 1 or 2 substituents which are selected from the group consisting of chlorine, methyl and trifluoromethyl;

$R'_2$ is a $C_{3-4}$ cycloalkyl group;

$R'_3$ is a hydrogen atom or represents 1 or 2 substituents which are selected from the group consisting of halogen, haloalkyl and haloalkoxy having 1–4 carbon atoms; and $R_4$ and $R_5$ are both fluorine atoms, or wherein $R_4$ is a chlorine atom and $R_5$ is a hydrogen atom.

2. A composition as claimed in claim 1, characterized in that the active constituent is N-(2,6-difluorobenzoyl)-N'-[4-(α-cyclopropyl-4-chlorobenzyloxy)phenyl]urea.

3. A method of controlling mites, whitefly and thrips, characterized in that the infected area is treated with a composition as claimed in any of claims 2 or 1 in a dosage from 10 to 5000 g of active substance per hectare.

* * * * *